US012486468B2

(12) United States Patent
Vecchini et al.

(10) Patent No.: US 12,486,468 B2
(45) Date of Patent: Dec. 2, 2025

(54) METHOD FOR THE PREPARATION OF OMEGA-AMINO-CARBOXYLIC ACIDS AND DERIVATIVES THEREOF

(71) Applicant: VERSALIS S.P.A., San Donato Milanese (IT)

(72) Inventors: Nicola Vecchini, Mantova (IT); Mirco Nodari, Mantova (IT); Armando Galeotti, Mantova (IT); Daniele Delledonne, Novara (IT)

(73) Assignee: VERSALIS S.P.A., San Donato Milanese (IT)

( * ) Notice: Subject to any disclaimer, the term of this patent is extended or adjusted under 35 U.S.C. 154(b) by 0 days.

(21) Appl. No.: 18/686,577

(22) PCT Filed: Aug. 9, 2022

(86) PCT No.: PCT/IB2022/057410

§ 371 (c)(1),
(2) Date: Feb. 26, 2024

(87) PCT Pub. No.: WO2023/026127

PCT Pub. Date: Mar. 2, 2023

(65) Prior Publication Data

US 2025/0136887 A1 May 1, 2025

(30) Foreign Application Priority Data

Aug. 25, 2021 (IT) ........................ 102021000022328

(51) Int. Cl.
*C10M 133/06* (2006.01)
*C07C 227/08* (2006.01)
*C10M 169/04* (2006.01)

(52) U.S. Cl.
CPC ......... *C10M 133/06* (2013.01); *C07C 227/08* (2013.01); *C10M 169/04* (2013.01); *C10M 2203/003* (2013.01); *C10M 2215/26* (2013.01)

(58) Field of Classification Search
CPC .............. C10M 133/06; C10M 169/04; C10M 2203/003; C10M 2215/26; C07C 227/08
See application file for complete search history.

(56) References Cited

U.S. PATENT DOCUMENTS

| | | | | |
|---|---|---|---|---|
| 5,773,665 | A | 6/1998 | Silverman et al. | |
| 5,880,072 | A | 3/1999 | Furey et al. | |
| 5,886,236 | A † | 3/1999 | Eisenschmid | |
| 5,973,208 | A | 10/1999 | Nagareda et al. | |
| 6,372,698 | B1 * | 4/2002 | Strothoff | C10M 133/06 508/459 |
| 6,946,580 | B2 | 9/2005 | Banister et al. | |
| 8,293,676 | B2 | 10/2012 | King et al. | |
| 8,377,661 | B2 | 2/2013 | Dubois | |
| 8,450,509 | B2 | 5/2013 | Dubois | |
| 8,697,401 | B2 | 4/2014 | Dubois | |
| 8,835,661 | B2 | 9/2014 | Couturier et al. | |
| 9,096,490 | B2 | 8/2015 | Couturier et al. | |
| 9,221,745 | B2 | 12/2015 | Couturier et al. | |
| 9,567,293 | B2 | 2/2017 | Dubois et al. | |
| 2011/0104764 | A1 * | 5/2011 | Dubois | C07C 227/08 562/553 |
| 2011/0105774 | A1 * | 5/2011 | Dubois | C07C 67/475 554/114 |
| 2012/0065110 | A1 * | 3/2012 | Kocsis | C10M 133/24 508/400 |
| 2014/0187808 | A1 * | 7/2014 | Couturier | C07C 227/04 554/114 |
| 2014/0323684 | A1 | 10/2014 | Dubois et al. | |
| 2015/0252290 | A1 † | 9/2015 | Snead | |
| 2016/0115120 | A1 † | 4/2016 | Dubois | |
| 2023/0391712 | A1 * | 12/2023 | Devaux | C07C 227/40 |
| 2024/0083838 | A1 * | 3/2024 | Devaux | C07C 227/08 |
| 2024/0140898 | A1 * | 5/2024 | Devaux | C07C 51/363 |

FOREIGN PATENT DOCUMENTS

| | | | |
|---|---|---|---|
| DE | 43 22 065 | A1 † | 1/1995 |
| EP | 0835924 | A1 † | 4/1998 |
| EP | 1151994 | A1 | 11/2001 |
| KR | 2020-0101801 | A † | 8/2020 |
| WO | 2008147704 | A1 | 12/2008 |

(Continued)

OTHER PUBLICATIONS

European Union Ecolabel application pack for lubricants, Version 1.1, Sep. 2014, www.smk.nl, 42 pages.
ATC Document 118, "Lubricant Additives: Use and Benefits", Aug. 2016, internet publication: https://www.atc-europe.org/public/Document%20118%20%20Lubricant%20Additives%20Use%20and%20Benefits.pdf.
Charmolue et al., "L-Serine Obtained by Methanol Addition in Batch Crystallization" American Institute of Chemical Engineers (AlChE) Journal, 1991, 37 (8), 1121-1128.
International Search Report and Written Opinion for International Application No. PCT/IB2022/057410, dated Nov. 8, 2022, 11 pages.
Mang, et al. (2011). "Lubricants, 1. Fundamentals of Lubricants and Lubrication". In Ullmann's Encyclopedia of Industrial Chemistry, vol. 21, pp. 383-389. doi:10.1002/14356007.a15_423.pub2.
Mang, et al. (2011). "Lubricants, 2. Components". In Ullmann's Encyclopedia of Industrial Chemistry, vol. 21, pp. 413-416. doi:doi:10.1002/14356007.015_004.

(Continued)

*Primary Examiner* — Ellen M McAvoy
(74) *Attorney, Agent, or Firm* — CANTOR COLBURN LLP

(57) ABSTRACT

A Method for the synthesis of ω-amino acids or derivatives thereof, includes the following steps synthesis of an ω-oxoester/linear acid by hydroformylation by $CO/H_2$ mixture of at least one monounsaturated acid/ester, the monounsaturated acid/ester preferably resulting from a reaction of metathesis of oils/fats from renewable sources; synthesis of a linear ω-amino acid/ester and/or ω-aminoamide, subjecting the aforementioned ω-oxoester/linear acid to reductive amination; and possible synthesis of a linear ω-amino acid, subjecting the aforementioned linear ω-aminoester and/or ω-aminoamide to hydrolysis.

21 Claims, No Drawings

(56) References Cited

FOREIGN PATENT DOCUMENTS

WO 2015027367 A1 3/2015

OTHER PUBLICATIONS

Morrison et al., Organic Chemistry, 6th Ed., 1992, Par. 20.17-20.18, pp. 773-778.
Morrison et al., Organic Chemistry, Fourth Edition, 1983, “Amines I. Preparation and Physical Properties”, pp. 906-908.
Perry’s Chemical Engineers’ Handbook, McGraw-Hill (7th Ed.—1997), Section 11, pp. 108-118.
Rodriguez, et al., “Tuning the Structure and lonic Interactions in a Thermochemically Stable Hybrid Layered Titanate-Based Nanocomposite for High Temperature Solid Lubrication”, in Adv. Mater. Interfaces 2017, 4, 1700047, 10 pages.
Waylin Lee Peddie, “Separation of Homogeneous hydroformylation catalysts using Organic Solvent Nanofiltration”, Thesis presented in partial fulfilment of the requirements for the Degree of Master of Engineering, University of Stellenbosch, Mar. 2016.
Widyarani, et al. “Fractional Precipitation of Amino Acids from Agro-industrial Residues Using Ethanol” Ind. Eng. Chem. Res. 2016, 55, 7462-7472.
Excerpt of the ECHA database for “Methyl 9-decenoate” last updated Jun. 12, 2024, 2 pages.
Third Party Observation for European Application No. 22757695.6, dated Jan. 29, 2025, 19 pages.
Wikipedia article “lubricant”, 12 pages.
Wikipedia article “one-pot synthesis”, 2 pages.
“One-pot synthesis” Wikipedia; This page was last edited on Jun. 2, 2025, at 17:47 (UTC).†
“Lubricant” Wikipedia; This page was last edited on Jul. 15, 2025, at 16:13 (UTC).†
ECHA Brief Profile for “Methyl dec-9-enoate”; fEC/List No. 662-772-0; CAS No. 256-41-6; Molecular formula: C11H2002; Updated Jun. 12, 2024.†

* cited by examiner
† cited by third party

METHOD FOR THE PREPARATION OF OMEGA-AMINO-CARBOXYLIC ACIDS AND DERIVATIVES THEREOF

CROSS-REFERENCE TO RELATED APPLICATIONS

This application is a 35 U.S.C. § 371 National Stage patent application of PCT/IB2022/057410, filed on 9 Aug. 2022, which claims the benefit of Italian patent application 102021000022328, filed on 25 Aug. 2021, the disclosures of which are incorporated herein by reference in their entirety.

TECHNICAL FIELD

The present disclosure relates to a process for the preparation of ω-aminocarboxylic acids or derivatives thereof and their use in the field of lubricants.

More specifically, the present disclosure relates to a method for the production of aliphatic ω-amino acids such as, for example, 11-aminoundecanic acid or 10-aminodecanoic acid, or derivatives thereof, starting from terminal monounsaturated carboxylic compounds, such as, for example, 9-decenoic or 8-nonenoic acid, preferably for applications in the field of lubricants, even more preferably in the field of biolubricants.

BACKGROUND

It is known that ω-aminocarboxylic acids, or derivatives thereof, can be used for applications in the field of lubricants, preferably in the field of biolubricants.

Lubricants are formulations based on base oils and additives that are applied in reducing friction between surfaces in diversified markets, such as automotive, industrial machinery or marine machinery. The differences in the applications and in the conditions of use are reflected in differences in the chemical formulation (selection and quantification of base oil and additives).

For example, it is reported in the literature that, in addition to the most important application in internal combustion engines, there are a vast number of other applications that often require specific lubricants: to meet the demand, over 90% of all applications, between 5,000 and 10,000 different formulations are needed.

In terms of volume, base oils are the most important component of lubricants, comprising more than 95% of the lubricant formulation: there are families of lubricants (e.g., some hydraulic and compressor oils) in which chemical additives account for only 1% of the formulation and the remaining 99% is base oil; on the other hand, some metalworking fluids may contain up to 30% of additives (Mang, T., Noll, S. and Bartels, T. (2011). *Lubricants, 1. Fundamentals of Lubricants and Lubrication*. In Ullmann's Encyclopedia of Industrial Chemistry, (Ed.). doi:10.1002/14356007.a15_423.pub2; Mang, T., Braun, J., Dresel, W. and Omeis, J. (2011). Lubricants, 2. Components. In Ullmann's Encyclopedia of Industrial Chemistry, (Ed.). doi: 10.1002/14356007.o15_o04).

For example, engine lubricants contain a number of additive components, which can range from 5 to 15, typically 8.

By way of example, an average composition, in mass percentage, of a car lubricant is made up as follows: base 77.6%, viscosity modifiers 10.9%, total additive content 11.5%. (Source: ATC DOCUMENT 118, August 2016, Table 5—internet publication: https://www.atc-europe.org/public/Document %20118%20%20Lubricant %20Additives %20 Use %20and %20Benefits.pdf)

In this context, WO 2015/027367 teaches that long-chain compounds (macromolecules) functionalised with two polar groups coordinate a polar group with each of the respective metal surfaces of a friction pair and, at the same time, the long chain makes the two metal surfaces completely separate, thereby preventing contact with each other, creating non-wearing friction and providing excellent anti-wear performance for the lubricating oil, unlike a traditional anti-friction modifier with a polar group at one end and an apolar hydrocarbon chain at the other.

EP 1151994A1 refers to new acid-succinimide compounds that can be used as lubricity additives, dispersants for lubricants, friction modifiers for lubricants, detergent additives for liquid fuels.

The succinoimide derivatives are prepared by reaction of a succinic acylating agent, substituted with aliphatic hydrocarbon groups, with amino acids or derivatives thereof. Amino acids suitable for the purpose include omega-amino acids such as, inter alia, 7-aminoheptanoic acid, 11-aminoundecanoic acid and 12-aminodecanoic acid. The acid succinimide compound is prepared by combining the hydrocarbyl substituted succinic acylating agent and at least one amino acid under appropriate operating conditions, easily determined by those skilled in the art.

This patent application does not specify the origin nor the preparation process of the starting amino acids.

WO 2008/147704A1 discloses a lubricating composition containing a lubricating viscosity oil, an oil-soluble molybdenum compound and a low-residue anti-wear agent. The patent application also relates to a new antioxidant. The lubricant composition can be used for internal combustion engines. The general formula of the low residue antiwear agent includes esters of D-amino carboxylic acids.

In U.S. Pat. No. 5,880,072, antiwear compositions are described comprising a cyclic amide and a monoester obtained from the reaction of a dicarboxylic acid with a polyol in substantially equimolar quantities, in which said dicarboxylic acid is a dimer of an unsaturated fatty acid. Preferred cyclic amides are lactams, produced by cyclization and removal of a water molecule from an □-amino acid. The cyclisation of amino acids to give lactams is known to those skilled in the art and is also reported in informative texts (https://en.wikipedia.org/wiki/Lactam).

In the publication by Gonzalez Rodriguez, P., et al., entitled "*Tuning the Structure and Ionic Interactions in a Thermochemically Stable Hybrid Layered Titanate-Based Nanocomposite for High Temperature Solid Lubrication*", in *Adv. Mater. Interfaces* 2017, 4, 1700047, a new solid, organic-inorganic nanocomposite lubricant is described, which synergistically combines the thermodynamically stable structure of a layered oxide with the relative flexibility of an organic polymer. This nanocomposite is made by intercalating 11-aminoundecanoic acid in a protonated titanate of the lepidocrocite type $H_{1.07}Ti_{1.73}O_4$.

Its use is also known for the production of polyamides and in processes for the production of polyamide 11 (PA11), in which the 11-aminoundecanoic acid, monomer, is mainly obtained from castor oil.

From the latter, through subsequent reactions involving thermo-oxidative demolitions, bromination and ammonia, the final synthesis of 11-aminoundecanoic acid is obtained.

At present, however, no alternative industrial methods have been found that allow for 11-aminoundecanoic acid to be obtained with a good yield, starting from a source other than that of castor oil, although numerous efforts have been made and, more generally, the alternative methods proposed for the synthesis of ω-amino acids can be complex and/or with a low yield, in the most favourable cases, for example, of around 50-60%. In fact, U.S. Pat. No. 8,377,661 describes a method for the synthesis of ω-amino acids or esters thereof starting from natural fatty acids.

The patent describes a process for the synthesis of amino acids or esters thereof through the conversion of natural monounsaturated fatty acids into unsaturated α,ω-diacids or diesters. This occurs through a homometathesis reaction or by fermentation to produce unsaturated diacids or diesters. The diacids or unsaturated diesters are then subjected to oxidative demolition at the level of unsaturation, in order to obtain individual acid-aldehydes. The acid-aldehydes are then converted into amino acids by reductive amination.

U.S. Pat. No. 8,450,509 describes a method for the synthesis of 9-aminonanoic acid or esters thereof from natural fatty acids. The method for the synthesis of amino acids or amino esters involves starting from long-chain unsaturated fatty acids or esters thereof. The fatty acids are subjected to cross metathesis with ethylene in order to form ω-unsaturated acids or esters. The ω-unsaturated acids/esters thus obtained can be subjected to oxidative demolition, to produce oxo-acids/esters, or, optionally, to be subjected to homometathesis to obtain an unsaturated, symmetrical diacid/diester which, in turn, by means of oxidative demolition, leads to the formation of oxo-acids/oxo-esters. A subsequent reduction in the oxo functionality of these compounds leads to the formation of the amino acid. U.S. Pat. No. 8,697,401 describes a method for the synthesis of amino acids or amino esters from monounsaturated fatty acids or esters thereof. The patent describes a method for the synthesis of amino acids starting from monounsaturated fatty acids or esters of natural origin. Also in this case, the process takes place in three stages: during the first, the unsaturated fatty acid is converted into unsaturated diacid through the homometathesis reaction. Subsequently, the unsaturated diacid is converted into unsaturated dinitrile by reaction with ammonia in the presence of zinc-based catalysts. In the second stage, the unsaturated dinitrile is converted into nitrile-acid/ester through oxidative demolition of the unsaturation by ozone. Optionally, a nitrile-acid/nitrile-ester with two more carbon atoms in the chain can be obtained by cross-metathesis reaction of the unsaturated dinitrile with acrylic acid. During the third stage, the nitrile-acid is converted to amino acid through reduction with hydrogen on Nickel Raney.

U.S. Pat. No. 8,835,661 describes a process for the synthesis of C11 and C12 ω-aminoalkanoic acids or esters comprising a nitrilation step. In an initial stage, the ω-unsaturated acid or ester of the fatty acid is subjected to nitrilation with ammonia, in the presence, however, of a Niobium-based catalyst, thus obtaining an ω-unsaturated nitrile. By cross-metathesis with acrylates, the unsaturated nitrile is converted into an unsaturated nitrile-ester, the reduction of which with hydrogen in the presence of palladium supported on carbon leads to the formation of the corresponding aminoester.

U.S. Pat. No. 9,221,745 describes a method for the synthesis of ω-amino acids or long chain esters (from 6 to 17 carbon atoms) comprising a cross metathesis step between an acrylic compound (acrylonitrile, acrylic acid, acrylic ester) and another nitrile/unsaturated acid/ester, in the presence of a Ruthenium carbene compound. The bifunctional unsaturated compound thus obtained (nitrile-ester or nitrile-acid) subsequently undergoes a hydrogenation process to obtain a saturated aminoester/amino acid.

US 2014/323684A1 describes a method for preparing saturated or unsaturated ω-amino acids comprising a hydroformylation step of an unsaturated nitrile obtained from cross-metathesis of fatty acids. The patent application describes the synthesis of amino acids through three stages: a first stage of hydroformylation of an unsaturated nitrile, a second stage of oxidation of the aldehyde-nitrile to produce acid-nitrile and a third stage of reduction of nitrile to obtain the amino acid. From the comparative example with methyl 10-undecenoate, it is clear that, under the given conditions, the hydroformylation of unsaturated nitriles produces conversion and selectivity to linear products greater than the similar unsaturated esters.

Published patent application US 2016/0115120A1 describes a method of synthesis of aldehydes from unsaturated nitrile/omega esters of fatty acids in which there is a specific control of the hydroformylation and isomerisation of unsaturated nitrile/omega esters of fatty acids. The patent application focuses mainly on the description of the parameters used in the hydroformylation reaction in order to maximise the ratio between linear and branched products.

U.S. Pat. No. 5,973,208 describes a process for the production of diamines starting from dialdehydes by reaction with ammonia and hydrogen, in the presence of a hydrogenation catalyst, of an alcoholic solvent and, optionally, of water.

In practice, as a first approximation, the various traditional synthetic ways of preparing ω-amino acids can be grouped into two classes: those relating to the use of multistage processes that mainly exploit the chemism of nitriles, however obtained, by direct nitrilation of acids or esters or by cross metathesis with acrylonitrile and those relating to consolidated processes involving a stage of regiospecific hydrobromination and then of substitution aliphatic nucleophilic of the Br group with $NH_2$.

Both classes present critical issues. In the case of the first class, it is emphasised that the nitrilation of acids or esters is a process that requires high temperatures, >250° C., with a high risk of isomerisation of the terminal double bond. Whilst the cross-metathesis with acrylonitrile of unsaturated compounds occurs only with low selectivity.

In the case of the second class, the criticality in the latter process lies precisely in the use of hydrobromic acid, which requires that the materials in contact are corrosion resistant and with excellent performance, as well as the management of important quantities of inorganic salts containing the bromide ion, as a by-product of ω-amino acid production.

Recently, new precursors have become available on the market, with the development of chemistry from renewable or biological sources.

It is therefore desirable to have new and flexible synthesis processes capable of using the various sources available on the market, starting, for example, from compounds with a variable number of carbon atoms to arrive at the same ω-amino acid.

Typically, for example, the synthesis of 11-aminoundecanoic acid (precursor of Nylon-11) is carried out starting from 10-undecenoic acid, by hydrobromination and subsequent amination, but it would be desirable to have a simple and convenient process to obtain the same industrially, also produced starting from products such as 9-decenoic acid or an ester thereof, which can be easily obtained from renewable sources by reaction of cross metathesis of unsaturated natural vegetable oils and fats with terminal olefins and potentially available in considerable quantities on a commercial scale.

The reactions described in most of the patents/patent applications mentioned above are combinations of: cross-metathesis, oxidative demolition, nitrilation, hydroformylation, reductive amination.

Specifically, amongst the reactions mentioned, the oxidative demolition reaction of the unsaturated C═C bond is particularly disadvantaged, as it uses toxic ozone as an oxidizing agent, with high generation costs. Ozonolysis is an industrial technology applied to productions in the pharmaceutical and speciality fields that do not require large quantities.

In the various syntheses described, preference is always given to the use of fatty acid nitriles to produce the final amino acid; nitriles, the preparation of which presents considerable criticalities for the operating conditions, as mentioned above.

Furthermore, although not always explicitly described in the patents/patent applications, all of the specified stages require intermediate purification and/or separation procedures. Given the multiple path options, the many parameters involved in the known reactions and the not entirely satisfactory conversion of the reactants and selectivity to the desired products, there is still a considerable margin for improvement of the process as a whole.

SUMMARY

The purpose of the present disclosure is therefore the creation of an innovative process for the synthesis of aliphatic ω-amino acids or their derivatives, starting from derivatives of linear chain ω-unsaturated carboxylic acids, preferably esters, more preferably esters of ω-carboxylic acids aliphatic unsaturated with 5 to 30 carbon atoms, even more preferably with a linear chain.

Specifically, an aim of the present disclosure is the preparation of 11-aminoundecanoic acid—which can, in turn, be used in the synthesis of polyamides—starting from methyl 9-decenoate (9-DAME) of renewable origin, limiting the number of intermediate purifications.

The Applicant therefore posed the problem of finding a process for the production of ω-amino acids starting from esters/monounsaturated fatty acids.

The Applicant has now found a method for the preparation of ω-amino acids starting from carboxylic compounds, preferably monounsaturated fatty esters comprising, in succession, the following reaction steps: hydroformylation of the monounsaturated compound, reductive amination of the oxo-derivative thus obtained, possible hydrolysis of the ω-aminocarboxylic compound thus produced to obtain the desired ω-amino acid, which can finally be subjected to a final stage of separation and purification to obtain the product in the form suitable for industrial use. This method can be carried out in batch or continuously; continuous mode is preferred.

Surprisingly, in fact, the Applicant has found that the aforementioned reactions can be carried out in series, by carrying out a single final purification stage without the process presenting critical issues, or requiring separation stages of the intermediates of the desired product from the other reaction products, to ensure an acceptable final purity of the desired product and a high yield and conversion into the desired product in each of the intermediate stages. This aspect therefore enables the simplification of the number of devices to be used and to considerably reduce the complexity of the overall process. Optionally, the use of intermediate purification stages can still be considered if it is appropriate to obtain semi-finished products and/or pure chemical intermediates.

These other purposes are surprisingly achieved by means of the preparation process according to the present disclosure.

DETAILED DESCRIPTION OF THE DISCLOSURE

Therefore, the present disclosure provides a process for the preparation of an ω-aminocarboxylic acid or a derivative thereof of formula (III)

$$H_2N—CH_2CH_2—CHR'-(Q)-COR'' \quad (III)$$

starting from an ω-unsaturated carboxylic compound with the following formula (I):

$$H_2C═CR'-(Q)-COR'' \quad (I)$$

wherein: R' is H or an aliphatic hydrocarbon group, possibly substituted, with 1 to 10, preferably from 1 to 5, carbon atoms and is, more preferably, H;

R" is an OR or $NR^1R^2$ group, preferably OR, wherein R is selected from between H, ammonium, a monovalent M metal, preferably an alkali metal, a C1-C15 alkyl group and a C6-C15 aryl group, preferably C1-C5 alkyl;

$R^1$ and $R^2$ are independently selected from between H, a C1-C15 alkyl group and a C6-C15 aryl group, preferably C1-C5 alkyl;

Q is a divalent, aliphatic, optionally substituted hydrocarbon group with 1 to 12 carbon atoms, preferably with 3 to 10 carbon atoms, more preferably linear, for example, a linear heptamethylene group or a linear hexamethylene group and, furthermore, said R' and Q groups can be linked together to form an aliphatic carbocyclic structure with 5 to 7 C atoms;

said process comprising the following stages in sequence:

(A) making said compound of formula (I) react under the hydroformylation conditions with a mixture of hydrogen and carbon monoxide in the presence of a suitable hydroformylation catalyst, preferably containing Rhodium or Iridium, based on Rhodium (1) or Iridium (1), preferably based on Rhodium (1), and phosphine binders and, optionally, a suitable solvent, to obtain the corresponding ω-oxocarboxylic derivative with the following formula (II):

$$OHC—CH_2—CHR'-(Q)-COR'' \quad (II)$$

with R', R" and Q correspondingly having the meaning specified above;

(B) subjecting said compound of formula (II) as obtained in step (A), preferably in the absence of intermediate purification steps of the compound of formula (II) from the other reaction products, with the exclusion of any recovery of the phosphine binder used, which precipitates by cooling from the solution, after evaporation of the eventual solvent and with the exclusion of the recovery of the eventual catalyst with one of the methods known by those skilled in the art, with reductive amination by reaction with hydrogen and ammonia in the presence of a suitable catalyst to obtain the ω-aminocarboxylic derivative of formula (III):

$$H_2N—CH_2—CH_2—CHR'\text{-}(Q)\text{-}COR'' \quad (III)$$

and separating it from any reaction solvent;

(C) optionally subjecting said compound of formula (III) to hydrolysis to obtain the corresponding ω-aminocarboxylic acid wherein R" in formula (III) is OH.

The ω-aminocarboxylic acid of formula (III) and/or its amino derivative of formula (III) synthesised as described above in accordance with the present disclosure can therefore be used directly:

as a friction modifier, in accordance with what is described in WO 2015/027367;

as a low residue antiwear agent and/or antioxidant agents, in accordance with what is described in WO 2008/147704;

as such, following intercalation in oxidic structures, in accordance with what described by Gonzalez Rodriguez et al.

The present disclosure also provides a lubricating composition containing, as an additive or base oil, a ω-aminocarboxylic acid of formula (III) and/or a derivative thereof of formula (III), produced preferably according to the process described above.

Specifically, if the ω-aminocarboxylic acid or a derivative thereof of formula (III), produced according to the process described above, is obtained from an ω-unsaturated carboxylic compound (1) of renewable origin, e.g., methyl 9-decenoate (9-DAME) obtained from the reaction of metathesis of vegetable oils and fats from renewable sources, the above composition will be a biolubricant, especially if the ω-aminocarboxylic acid or a derivative thereof of formula (III), produced according to the process described above, constitutes the base oil of said lubricating composition (biolubricant).

In fact, the base oil generally constitutes the largest share of the total lubricant composition, generally at least 70-80% in lubricants for internal combustion engines.

Preferably, the lubricant according to the present disclosure must contain at least one percent (1%) of carbon from renewable raw materials on the whole formulation and/or at least 25%, preferably 50%, of carbon from renewable raw materials on a single component (base and/or, viscosity modifiers and/or additives) from ω-aminocarboxylic acid or a derivative thereof of formula (III).

The carbon content from renewable raw materials is estimated with one of the methods known to those skilled in the art, for example, as reported on page 23 of 42 of the European Union Ecolabel Application Pack For Lubricants—Version 1.0—September 2011: the carbon content of the lubricant is given by multiplying the renewable fraction of each component (C atoms from vegetable and animal oils and fats divided by the total number of C atoms (C atoms from vegetable and animal oils and fats AND C atoms from petrochemical origin) multiplied by the fraction of competence.

According to the present disclosure, the term ω-aminocarboxylic acid means an organic compound comprising a carboxylic group —COOH, and an aminoethyl group $—CH_2—CH_2—NH_2$, wherein said carboxylic group and said aminoethyl group are spaced by at least 2 carbon atoms, preferably at least 4 carbon atoms.

Preferably, said carboxyl group and said aminoethyl group are spaced by a chain of from 5 to 15 carbon atoms, more preferably, by a linear chain of formula $—(CH_2)_r—$, with r being an integer from 5 to 15.

In accordance with the present disclosure, the term "derivative of an ω-amino carboxylic acid" refers to any compound that can be obtained from a ω-carboxylic amino acid, wherein the carboxylic group —COOH is replaced by a carboxylate salt group —COOM' with M'=ammonium or alkali metal, ester —COOR, amide $—CONR^1R^2$, with R, $R^1$ and $R^2$ having the general and preferred meanings previously specified.

In accordance with the present disclosure, with the indefinite singular articles a and one, the meaning of at least one, is also understood, unless otherwise specified.

In accordance with the process according to the present disclosure, in step (A), a controlled catalytic hydroformylation reaction is carried out to obtain a carboxylic ω-oxo-derivative of formula (II) with high yields and with a l/b ratio (linear/branched) high (ratio between the desired oxo-derivative and its eventual branched or further branched isomers if the compound of formula (I) already comprises branched alkyl chains) starting from an ω-unsaturated carboxylic derivative of formula (I), preferably an ester, more preferably a linear aliphatic carboxylic ester, by reaction with syngas (hydrogen/carbon monoxide mixture) in the presence of a suitable hydroformylation catalytic system, preferably based on Rhodium and a bidentate phosphine ligand.

The molar ratio $H_2/CO$ in the syngas is chosen by those skilled in the art according to what is known in the field of hydroformylation of primary olefins, preferably between 0.3 and 3, more preferably between 0.8 and 1.3, for example, approximately 1.

Compared with the prior art, step (A) is distinguished by the favourable operating conditions in terms of the composition of the reaction mixture and reaction times, necessary to obtain in high yields the (preferably linear) ω-oxoester product of interest.

The reaction is typically carried out at temperatures of between 6° and 140° C. and under pressures of between 1.5 and 6 MPa, for times that can range, depending on the substrate of formula (I), temperature and pressure, from 0.5 to 24 hours, preferably from 1 to 3 hours.

The reaction can be carried out on the pure compound of formula (I) or in the presence of a suitable quantity of organic solvent, preferably between 5 and 90% by weight with respect to the total of said reaction mixture.

Said organic solvent can be, for example, a polar solvent such as a linear, branched or cyclic ether, such as, for example, methyl tert-butyl ether (MTBE), or an alcohol with 1 to 6 carbon atoms such as methanol or ethanol or an aromatic solvent such as benzene, toluene, xylenes, ethylbenzene, or an aliphatic hydrocarbon such as heptane or cyclohexane.

Preferably, the solvent is selected from the aforementioned classes of compounds in such a way that it is able to solubilise, in the reaction environment, the phosphine binder, the compound of the metal M and the substrate of formula (I) itself.

Furthermore, the solvent is preferably lower-boiling than the compounds of formula (I) and (II) so that it can be separated from these, at least in part, by evaporation.

Preferred solvents are ethanol, methanol, MTBE and toluene.

If the organic solvent is an alcohol (such as methanol), at the end of the hydroformylation reaction, an acid hydrolysis step of the acetal derived from the ω-oxocarboxylic compound of formula (II) is preferably carried out, in the manner known in those skilled in the art, to give the corresponding aldehyde group.

In accordance with the present process, all known catalytic systems suitable for the purpose, on which a large amount of literature is available, can be used as hydroformylation catalysts.

Specifically, a suitable catalyst for hydroformylation comprises a precursor consisting of a salt or a soluble complex of a metal M selected from Rhodium, Cobalt, Iridium, Ruthenium, preferably Rhodium (Rh) and Iridium, more preferably Rhodium, and a ligand L, preferably a phosphine binder, more preferably an aromatic phosphine, especially a bidentate aromatic phosphine. The metal M, especially Rh, in said complexes is preferably in a low oxidation state, for example Rh (I).

Rh salts typically usable in step (A) of the present process are those normally used in the art to hydroformylate the primary olefinic group, such as, for example, $HRh(CO)(PPh_3)_3$, $(acac)Rh(CO)_2$, $[Rh(COD)Cl]_2$, $RhCl(PPh_3)_3$, preferably, $(acac)Rh(CO)_2$ (where acac=acetylacetonate and COD=1,5-cyclooctadiene).

The phosphine ligand L in the hydroformylation catalyst is preferably a bidentate (two P atoms per molecule capable of coordinating M) or polydentate (more than two P atoms capable of coordinating M), more preferably bidentate. It can be bonded to the metal M in a preformed metal complex and/or it can be added in the same reaction environment in which the salt of M is found, for example, Rh.

Preferably, the ligand L, particularly when it is a phosphine ligand, is present in strong molar excess with respect to M, preferably with an L/M ratio of between 2 and 40, more preferably of between 4 and 20.

Phosphines that can be used for this purpose are aromatic phosphines and polyphosphines, such as, for example, phosphines with general formulae $[P(X^1)(X^2)(X^3)]_m$, wherein $X^1$, $X^2$ and $X^3$ independently represent preferably aryl or aryloxy groups, substituted or unsubstituted and possibly linked together for values of m greater than 1 and m=1 in the case of monophosphines, m=2 in the case of bidentate phosphines, m>2 (normally 3 or 4) in the case of polidentate phosphines.

Typical bidentate phosphine ligands, suitable for the process of the present disclosure, are the following, the most commonly known name in English of which is transcribed for convenience:

BISBI: [1,1'-bis(diphenylphosphinomethyl)-2,2'-biphenyl];

Naphos: [2,2'-bis(diphenylphosphinomethyl)-1,1'-binaphthyl];

Xantphos: [4,5-bis(diphenylphosphino)-9,9-dimethylxanthene];

BiPhePhos: [6,6'-[(3,3'-Di-tert-butyl-5,5'-dimethoxy-1,1'-biphenyl-2,2'-diyl)bis(oxy)]bis(dibenzo[d,f][1,3,2]dioxaphosphepin)];

DPEphos: [bis(2-diphenylphosphinophenyl)ether];

DBFphos: [4,6-Bis(diphenylphosphino)dibenzofuran].

Preferred phosphines are specifically Xantphos and BiPhePhos; even more preferably BiPhePhos, with the following structural formula:

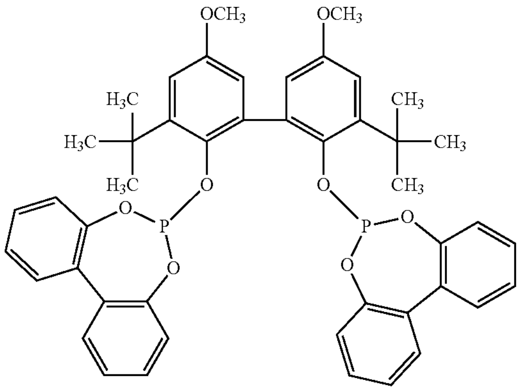 [SMILES: COc1cc(-c2cc(OC)cc(C(C)(C)C)c2Op2oc3ccccc3c3ccccc3o2)c(Op2oc3ccccc3c3ccccc3o2)c(C(C)(C)C)c1]

Conveniently, the catalytic molar ratio between the substrate to be hydroformylated (compound of formula I) and metal M in the catalyst, preferably Rh, is between 1,000 and 500,000, but can also extend beyond these limits.

One of the sensitive aspects of the hydroformylation reaction in step (A) of the present disclosure is represented by the selectivity towards the ω-oxo-derivative product of formula (II), with respect to the product isomerised by migration of the olefinic double bond from primary to internal.

Selectivities higher than 95% are usually obtainable with the best catalysts known in the art, with l/b ratios (linear/branched) for linear molecule compounds, higher than 5, preferably higher than 20.

For example, the hydroformylation of methyl 9-decenoate with a mixture of $CO/H_2$=1:1 at 4.5 MPa in toluene, or MTBE, or methanol, in the presence of a catalytic mixture consisting of a precursor based on Rhodium, (acetylacetonate) dicarbonylrhodium (I), and BiPhePhos, ester/Rh ratio=7500, BiPhePhos/Rh ratio=8, temperature=100° C., leads to complete conversion of the unsaturated ester, yield to hydroformylation products of 79% and ratio l/b between linear and branched ω-oxoester equal to 55 within 2 hours of reaction.

The compound of formula (II) obtained in step (A) can be purified from the reaction mixture that contains it, which includes the by-products, the catalyst and/or residues thereof, the phosphine and any solvent.

However, the Applicant has surprisingly found that this step of separation and purification of the intermediate compound of formula (II) from the other reaction by-products cannot be carried out if the subsequent step is a reductive amination, with the exception of

- a possible partial removal of the solvent by evaporation in order to avoid excessive dilution;
- the recovery of the binder by precipitation and separation of the phosphine for its reuse in the process;
- the recovery of a large part of the catalyst obtained by means of one of the methods known to those skilled in the art such as, for example, the distillation of the hydroformylation products from the catalyst or by nanofiltration of the catalyst from the hydroformylation products (*Separation of Homogeneous hydroformylation catalysts using Organic Solvent Nanofiltration* by Waylin Lee Peddie, Thesis presented in partial fulfilment of the requirements for the Degree of MASTER OF ENGINEERING, University of Stellenbosch) or by absorption on ionic resins in acid form, as described for example in U.S. Pat. No. 5,773,665;

and the entire reaction mixture can be directly transferred to the reductive amination stage (B), without any particular interference. In this way, a costly separation and purification procedure from the hydrogenated and branched by-products is avoided.

In the subsequent stage (B) of the process according to the present disclosure, the ω-oxo-derivative of formula (II) obtained from step (A), preferably without being separated from the reaction mixture, except for a possible partial evaporation of the solvent and/or possible recovery of the phosphine binder used and/or recovery of the catalyst, is subjected to reductive amination to convert it into the corresponding ω-aminocarboxylic acid derivative of formula (III).

The reductive amination of step (B) is a reaction already known and reported in the literature for a multiplicity of substrates and widely used in the synthesis of amines starting from aldehydes (see, for example, Morrison, Boyd—Organic Chemistry pages 906-908 IV Edition). In U.S. Pat. No. 8,377,661, it is carried out at a hydrogen pressure between 100-150 atm for a time of 4 h using Ni Raney as catalyst.

Suitable reductive amination catalysts for the purposes of the present disclosure are commercial or synthetic hydrogenation systems, based on one or more metals of groups 8, 9 and 10 of the periodic table, such as, for example, Iron, Cobalt, Nickel, or noble metals such as Ruthenium, Rhodium, Palladium, Osmium, Iridium or Platinum, preferably Cobalt, Nickel, Palladium and Platinum.

These catalysts can be used in dispersed, colloidal, spongy (e.g., Raney Ni) or supported/bound phase, preferably in supported/bound form on inorganic phase with high surface area, even more preferably in supported/bound phase on silica, alumina or silica-alumina.

In accordance with step (B) of the present process, therefore, the reductive amination of the compound of formula (II) is carried out using a reduction catalyst based on a metal with hydrogenating characteristics of groups 8, 9 or 10 of the periodic table, preferably selected from between Nickel, Cobalt, Palladium and Platinum, with a mixture of ammonia and $H_2$ in molar ratio $NH_3/H_2$ of between 5 and 25, in the presence of water in molar ratio $H_2O/NH_3$ of between 0.01 and 0.25.

The reaction is carried out in excess of ammonia with respect to the ω-oxo-derivative, preferably with a molar ratio $NH_3$/(compound (II) of between 30 and 60.

The reaction temperature is between 3° and 200° C., preferably between 5° and 150° C. and the pressure is between 3 and 15 MPa, more preferably between 6 and 9 MPa.

The ω-oxoester reductive amination reaction can be carried out in batches (in a reactor equipped with stirrer, heating jacket and inlets for gases and liquid streams) for a reaction time of between 0.1 and 3.0 h, preferably of between 0.5 and 1 h. Or it can be carried out continuously, for example, in a tubular reactor with one or more stages. The continuous mode is preferred for productivity issues, especially on an industrial scale.

The reductive amination occurs by reaction of the ω-oxo-derivative (II) with ammonia in a hydrogen atmosphere and in the presence of a reduction catalyst.

The reductive amination reaction can be carried out in the presence of an organic solvent, preferably selected from between methyl tert-butyl ether, methanol, ethanol and isopropanol.

In the preferred case in which the compound of formula (II) is a linear ω-oxo-derivative, the main reductive amination product is the corresponding linear ω-amino-derivative (III), obtained predominantly with respect to the branched amino-derivatives.

The formation of the corresponding aminoamides is also observed, amongst which the most abundant is the linear ω-aminoamide. However, these compounds are desirable as they also produce the desired ω-carboxylic amino acid at the end of step (C) of hydrolysis.

The ω-amino-derivative of the carboxylic acid of formula (III), obtained in step (B) of the present process, can optionally be subjected to hydrolysis for the synthesis of the corresponding amino acid, unless R" is already OH, or be used as such after a purification step according to the techniques most suitable for the purpose, for example by extraction in an aqueous acid environment with a pH of between 4 and 7 and subsequent neutralisation. If, on the other hand, the desired compound is the corresponding ω-aminocarboxylic acid, this being the preferred aspect, the process of the present disclosure comprises an optional step (C) of hydrolysis, in particular, in cases wherein R" in the compound of formula (III) is an ester or amide group (R"=OR or R"=$NR^1R^2$, with R alkyl or aryl and $R^1$ and/or $R^2$ regardless of H, alkyl or aryl) carried out under conditions selected by the Applicant to optimise the yield in the desired product and, furthermore, still without the need to separate the compound of formula (III) from the reaction mixture of step (B).

The hydrolysis of esters or amides is a reaction widely known in the literature and which can be carried out in various ways by the expert in the field, both with alkaline and acid catalysis (Morrison, Boyd—Organic Chemistry, 6th Ed., Par. 20.17-20.18). The methods described below therefore refer to the conditions used by the Applicant.

The hydrolysis reaction of the ω-amino-derivative of formula (III) with R" as specified above, preferably linear, is carried out with water in the presence of an acid catalyst such as hydrochloric acid, or basic such as sodium hydroxide. Basic hydrolysis is preferred.

Even the aminoamides, under the same reaction conditions, give hydrolysis leading to the obtaining of the corresponding amino acid, helping to increase the overall yield of the process.

The hydrolysis is preferably carried out hot, preferably at between 4° and 120° C., even more preferably at the boiling temperature of the reagent mixture, continuously removing the alcohol (such as methanol) produced during the hydrolysis of the ester bond and/or the organic solvent used in the previous reductive amination step; if a basic catalyst is used, it is possible to operate in boiling and partial condensation of the vapours in reflux mode.

The basic catalyst is always necessary if the compound of formula (III) is an alkylamide of ω-aminocarboxylic acid ($R^2$=—NR'R" in formula (II)).

Hydrolysis is carried out in a stoichiometric excess of water; this excess of water can be guaranteed at the beginning of the reaction or during the same through additions by entering from a special line. The main product of hydrolysis is the desired ω-amino acid, preferably linear.

If requested by the end users, the preferably linear ω-amino acid thus obtained, or its derivatives before the hydrolysis step (C), can be separated from the impurities constituted by the corresponding branched isomeric amino acids using one of the methods already known in the art, for example by fractional crystallisation. However, in most cases, this separation can be omitted given that the process of the present disclosure advantageously allows for very high l/b (linear/branched) ratios to be obtained and in accordance with the requirements for subsequent uses of the product.

In the patents of the prior art that use nitriles as reagents (for example, US 2014/0323684, U.S. Pat. Nos. 9,567,293; 9,096,490), nitriles are produced by reaction with anhydrous gas ammonia at a temperature ranging from 300° C. to 600° C. Subsequently, the nitrile acids/esters obtained require a further reduction reaction with hydrogen to obtain the corresponding amino acids/amino esters.

In the process of the present disclosure, however, the aminoreduction step already allows for the amino-derivative/amino acid of interest to be obtained at temperatures of between 8° and 120° C. and in a single step.

The process in accordance with the present disclosure is also advantageous with respect to the state of the art that uses nitriles, the production of which includes the use of hydrogen cyanide. In this case, in fact, whilst not performing amination, it is always necessary to reduce the nitrile with hydrogen to obtain the corresponding amino acid/aminoester. Furthermore, the use of hydrogen cyanide presents much greater risks than the use of ammonia according to the present disclosure.

Preferably, in the process of the present disclosure, no intermediate purifications of the reaction mixtures obtained in stages A) or B) are carried out, but only possible solvent evaporations for the recovery and use thereof and the procedures for the recovery of the catalyst according to one methods known to those skilled in the art.

In this regard, different solvents can be used, such as, for example, toluene for the hydroformylation stage and methanol for the second reductive amination stage.

However, the Applicant has surprisingly identified the possibility of using a single solvent for both reaction stages, further simplifying the process.

This solvent can be chosen from within the class of ethers; specifically, the use of methyl tert-butyl ether (MTBE) as the only reaction solvent for stages (A) and (B) of the process has proved particularly suitable for this purpose.

In the present process, all the reaction stages and the final purification stage can be carried out continuously.

Specifically, the use of a single solvent for the hydroformylation and reductive amination reactions further simplifies the process making it, in the continuous configuration, even more efficient in terms of productivity and operating costs.

The possibility of using a single integrated process for the synthesis of ω-amino acids starting from ω-unsaturated esters or amides, nor the possibility of using a single solvent for the hydroformylation and reductive amination, have been previously described in any of the methods of the prior art.

The separation/purification step of the ω-carboxylic amino acid, preferably linear, following the hydrolysis step (C), includes, if this is carried out in a basic environment, the acidification of the hydrolysed mixture up to a pH value of between 3 and 9, preferably of between 5 and 7, with consequent precipitation of the product of interest.

Precipitation by pH correction can be carried out both under hot, cold and at room temperature. Cold precipitation, by refrigeration at 5-10° C., is preferred.

The ω-aminocarboxylic acid, preferably linear, thus precipitated, is separated from the mother liquors by any liquid-solid separation method suitable for the purpose, for example, by filtration and/or centrifugation. The purification of the product thus separated takes place using the normal techniques known to the expert in the field, for example, by subsequent washing. Washing first with water and then with an organic solvent is preferred. The use of acetone or ethyl acetate are particularly preferred as organic solvents.

The product purified to the desired degree, possibly obtained by iterating washing cycles with water and organic solvent, is lastly dried using the normal techniques known to those skilled in the art, such as flushing with inert gas, heating under vacuum or by lyophilisation.

In a particularly preferred embodiment of the present disclosure, the Applicant found a new and original process for the production of 11-aminoundecanoic acid starting from methyl 9-decenoate (9-DAME), said 9-DAME specifically obtained from metathesis reaction of vegetable oils and fats from renewable sources.

The process in accordance with the present disclosure is therefore described below in greater detail with reference to the production of 11-aminoundecanoic acid starting from 9-DAME, without, however, it being understood in any way in a limiting sense towards the application of the same inventive process with omega-unsaturated carboxylic compounds (salts, acids, amides, esters) with a different structure and different number of carbon atoms, within the limits of the previous formula (I).

The mixture of 9-DAME and MTBE solvent is fed continuously, after the addition of the Rhodium-based catalyst and the phosphine binder, to a CSTR or tubular type reactor with recirculation. A preferred solution is that based on a CSTR reactor fitted with an apparatus that facilitates contact between liquid and gas, for example, a liquid jet ejector located on the upper bottom, with a circulation pump that feeds the liquid reagent mixture to the ejector and promotes mixing of the reactant phase contained in the reactor. A further preferred solution is that which provides two reactors with these characteristics, placed in series. The hydroformylation reaction takes place at a temperature of between 6° and 140° C., preferably at between 8° and 120° C., even more preferably at between 10° and 110° C., for a residence time of between 0.5 and 24 h, preferably between 1 and 3 h. 9-DAME can also be fed in the absence of solvent, although the mixture in solvent is preferred. Said solvent may be present by up to 90% by weight with respect to the entire solution, preferably from 5 to 70%, more preferably from 30 to 60% by weight with respect to the entire solution.

The gaseous mixture of hydrogen and carbon monoxide (syngas) used for the hydroformylation reaction has a molar composition of between 3 parts of hydrogen per 1 part of carbon monoxide and 1 part of hydrogen per 3 parts of carbon monoxide, preferably consisting from 1 part of hydrogen to 1 part of carbon monoxide in moles. The syngas pressure at which the reaction is carried out is between 1.5 and 6 MPa (15 and 60 bar), preferably between 3 and 5 MPa.

The hydroformylation catalyst is preferably a metallorganic Rhodium complex, prepared in situ by the reaction of a precursor of Rhodium, preferably (acetylacetonate) dicarbonylrodium (1) and of a bidentate phosphine ligand, preferably BiPhePhos (where BiPhePhos refers to the molecule "6,6'-[(3,3'-Di-tert-butyl-5,5'-dimethoxy-1,1'-biphenyl-2,2'-diyl)bis(oxy)]bis(dibenzo[d,f][1,3,2]dioxaphosphepine)" with a molecular weight of 786.78 Da. The molar ratio between 9-DAME and the Rhodium precursor is between 2,500 and 20,000, preferably between 5,000 and 15,000. The molar ratio between the bidentate phosphine ligand and the Rhodium precursor is preferably between 2 and 40, more preferably between 4 and 20.

The main hydroformylation product, linear ω-oxoester, is obtained with yields of up to 80%. The conversion of the unsaturated ester is between 73 and 99.9%, the selectivity towards hydroformylation products (linear, more branched) between 60 and 99%, the selectivity towards linear hydroformylation products—expressed as linear/summation ratio of branched hydroformylation products, l/b—is greater than 25.

All conversion, selectivity and yield values mentioned refer to those determined by gas chromatographic analysis of the reaction mixtures in the presence of internal standard as described in the examples (internal standardisation).

The stream leaving the reactor is depressed in a gas-liquid separator and the liquid fraction is cooled (with the possibility of partial heat recovery) in order to recover part of the phosphine binder which separates as a solid from the liquid stream. The separation of the solid can be conveniently carried out in a gravity separator or in a centrifugal separator. The set-up based on a continuous horizontal centrifugal separator is the preferred set-up. The clarified liquid phase is sent to the next stage of separation of the desired product, whilst the solid is recycled in input to the hydroformylation reactor. In this way, the phosphine binder can be recovered for its reuse in the process.

The clarified liquid stream can optionally be fed to an evaporator to recover the solvent and any unreacted 9-DAME. Any type of evaporator known in the art can be advantageously used for the purpose of the present disclosure. Preferably, a "kettle" type evaporator is used. Further details on the types of evaporators that can be used for this purpose can be found, for example, in Perry's Chemical Engineers' Handbook, McGraw-Hill (7th Ed.—1997), Section 11, pages 108-118. An alternative set-up is based on the use of a flat or filled distillation column. The distillation column allows for the recycling of the solvent and any unreacted 9-DAME, with a lower content of products of the hydroformylation reaction than in the case of using an evaporator.

The liquid stream exiting the evaporator, or from the bottom of the distillation column, which contains the hydroformylation products and the catalyst, can in part be recycled to the hydroformylation for the recycling of the catalyst and in part be sent to the section for the removal of the catalyst which can take place with one of the methods known in the literature and to those skilled in the art, such as, for example, the method described in U.S. Pat. No. 5,773,665 (ELF Atochem) or U.S. Pat. No. 6,946,580 (Davy process Technologies).

The liquid stream, deprived of the catalyst and any binder, is then sent to an exchanger and heated to a temperature of between 30° C. and 200° C., preferably of between 80° C. and 140° C., more preferably of between 100° C. and 110° C.; said current coming from said exchanger is sent to a reactor for the reductive amination reaction; said reactor is preferably a fixed bed, more preferably in a "trickle bed" configuration, operating at a WHSV (Weight Hourly Space Velocity, relative to the entire reagent mixture) of between 1 and 50 $h^{-1}$, preferably of between 3 and 10 $h^{-1}$. Said reactor is equipped with a thermostating system and contains a hydrogenation catalyst. The preferred hydrogenation catalyst is of the commercial type based on Cobalt or Nickel, preferably supported on alumina or silica/alumina. Said reactor is fed with liquid ammonia. The reaction is carried out in excess of ammonia with respect to the ω-oxoester, with a molar ratio between ammonia and ω-oxoester of between 15 and 70, preferably of between 30 and 60.

The reductive amination reaction can be carried out in the presence of an organic solvent, preferably selected from between methyl tert-butyl ether, methanol, ethanol and isopropanol. Methyl tert-butyl ether is preferred. Said solvent can be present from 5% to 90% by weight with respect to the reaction mixture, preferably from 30 to 70%, more preferably at 50% by weight with respect to the reaction mixture.

The reductive amination reaction is preferably carried out in the presence of water, in an amount of between 2 and 10% by weight with respect to ammonia; said reactor is also fed with $H_2$ up to a pressure of between 0.3 and 30 MPa (3 and 300 bar), preferably of between 3 and 15 MPa (30 and 150 bar), more preferably of between 6 and 9 MPa (60 and 90 bar). The reactor is kept flushed in gas by recycling the gas leaving the reactor head to the bottom of the reactor by means of a compressor/fan. A part of fresh ammonia is fed continuously in order to maintain the molar ratios specified above. A part of the recovery $H_2$ is fed in order to maintain the pressure values specified above. A stream consisting of the mixture of reaction products and, optionally, the solvent comes out of the bottom of the reactor. A preferred set-up of this reactor is one which involves recycling the excess gas, specifically ammonia, through the use of a liquid jet ejector that is installed on top of a "trickle bed" type reactor. The motive liquid is the same reaction mixture that is recirculated through a pump.

The main product of reductive amination is the linear ω-aminoester (methyl 11-aminoundecanoate); the main by-product is the reductive amination product of the aldehyde group and the contextual amidation of the ester group, namely ω-aminoamide; this compound is, however, of interest as it also produces, at the end of the subsequent hydrolysis stage, the desired ω-amino acid. The ω-oxoester conversion is quantitative, the selectivity towards aminoesters is higher than 88% and the selectivity towards amination-amidation products (ω-aminoamides) is lower than 12%. All conversion, selectivity and yield values mentioned refer to those determined by gas chromatographic analysis of the reaction mixtures in the presence of internal standard.

Said current can be suitably sent to a system for the recovery of dissolved ammonia and solvent. The preferred set-up is that based on a degasser where the reaction mixture undergoes, after pressure reduction down to 0.1-2.0 MPa (1÷20 bar), preferably 0.3-0.8 MPa (3÷8 bar), even more preferably at 0.4-0.6 MPa (4÷6 bar), a partial vaporisation with passage to the vapour phase of most of the dissolved ammonia and part of the solvent. The liquid exiting the degasser is fed to an evaporator for the recovery of the solvent. The reaction mixture with traces of solvent comes out from the bottom of the evaporator. The vapour deriving from the evaporator is fed to the degasser, which contains some perforated plates that serve to facilitate both the separation and the contact of the two phases: the liquid phase and the vapour phase. The vapour phase that comes out of the degasser is partially condensed in a first condenser of the reflux type, which operates at a temperature of 20-250° C., preferably at 80-150° C., even more preferably at 105-130° C. and, subsequently, in a post condenser operating at a temperature of −75-80° C., preferably at −20-30° C., even more preferably at −5-15° C. The liquid that collects at the outlet from the condenser is the solvent that is recycled, whilst the liquid exiting the post-condenser is mainly made up of ammonia that is, in turn, recycled.

The mixture exiting the evaporator can be sent to hydrolysis stage C): however, in a preferred configuration, it is first sent to a further degasser which is at an absolute pressure of between 10 and 400 kPa, preferably of between 50 and 250 kPa, for example, 80 kPa absolute. In this further degasser the residual solvent content is reduced to less than 1%, preferably to less than 0.1%, even more preferably to less than 0.01% by weight. The vapour that separates in this degasser is condensed at a temperature of −75-80° C., preferably of −20-30° C., even more preferably at −5-15° C. and is then recycled to the first degasser. The hydrolysis of esters is a reaction known in the literature that can be carried out in various ways by the expert in the field. The methods specified below therefore refer to the conditions used by the Applicant and are in no way to be considered as limiting the process of the present disclosure.

The hydrolysis takes place continuously in a reactor, called hydrolyser, preferably of the CSTR type, fitted with a heating system and a condensing system formed by a partial reflux condenser, which recycles the water in the hydrolyser and a post-condenser which condenses most of the methanol that is produced and that constitutes a co-product of the process, in the presence of a basic catalyst, preferably sodium hydroxide or potassium hydroxide, for a residence time of between 0.5 and 12 h, preferably of between 2 and 6 h. If necessary, the pH of the solution is maintained at values >12 by adding NaOH or KOH. The hydrolysis is carried out hot, preferably at the boiling temperature of the mixture. The hydrolysis products come out from the bottom of the reactor; the main product is ω-linear amino acid, obtained predominantly with respect to branched amino acids. Optionally, the solution leaving the hydrolysis reactor can be sent first to a static separator thermostated at the hydrolysis temperature. Part of the by-products are removed from the top of the separator; an aqueous stream is obtained from below to be sent to the separation section of the product of interest, by means of precipitation/crystallisation.

To said aqueous stream, containing the hydrolysis product of interest, acid is added so as to adjust the pH to a value of between 3 and 9, preferably of between 5 and 7. The acid can be anhydrous or in solution HCl, or acetic acid; the HCl in solution is preferred. Said solution is cooled to a temperature of between 2 and 20° C., preferably of between 5 and 10° C. and is then sent to a mixed tank where the product forms a precipitate which is kept in the liquid phase to form a cloudy mixture or "slurry", which is subsequently sent to a filtration and washing system of the solid, formed by the O-linear amino acid, which constitutes the final product of the process.

The purification of the ω-amino acid after it has been thus separated can be carried out with the normal techniques known to the expert in the field. For example, it can be carried out by recrystallization, washing with one or more liquids in which it is not very soluble, electrophoresis, etc. For example, the ω-linear amino acid can be purified by cold washing first with water and then with an organic liquid in which it is poorly soluble (preferably less than 1 g/l solubility), for example, a ketone, such as acetone or butanone, an alcohol, such as methanol or ethanol, an ester, such as ethyl acetate, butyl acetate, etc. Acetone and ethyl acetate are preferred. The white solid obtained is conveniently dried by one of the known techniques suitable for the purpose, such as flushing with inert gas, heating under vacuum or freeze-drying.

The organic washing liquid is recovered by distillation in the column, obtaining the high-boiling compounds and impurities from the top and bottom. For the crystallization/sedimentation and filtration operations, it is possible to use what is already present in the prior art, such as for example in the articles published in "*Industrial & Engineering Chemistry Research,* 2016, 55, 7462-7472" or in "*American Institute of Chemical Engineers* (*AIChE*) *Journal,* 1991, 37 (8), 1121-1128".

The purity of the linear ω-amino acid is determined by gas chromatographic analysis (GC-FID) after silylation of the product according to one of the methods known to those skilled in the art.

As mentioned, ω-aminocarboxylic acid of formula (III) or a derivative thereof of formula (III) obtained with the process of the present disclosure can be conveniently used for the preparation of lubricating compositions, for example according to what is known in the art regarding the use of ω-aminocarboxylic acids as such or in compounds derived therefrom, for example, by oligomerisation, cyclisation (e.g., lactam formation) and other functionalisation reactions described in the art, for example, by reaction with a succinic acylant substituted with aliphatic hydrocarbon groups.

Examples of derivative compounds which can be advantageously obtained from ω-aminocarboxylic acids according to the disclosure are the compounds S Acid-8, S Acid-6, S Amide 1, S Amide5, S Amide9, S Amide10, S Ester 7, S Ester 8, S Ester 4, which contain 11-aminoundecanoic acid derivatives as their characteristic part and already recognised in the art, for example, in EP 1151994, as lubricants or lubricant additives.

The present disclosure further provides a method for the preparation of a lubricating or biolubricating composition comprising the preparation of a ω-aminocarboxylic acid of formula (III) or a derivative thereof of formula (III), in accordance with the previously described process and in addition the additional and subsequent stage of introducing said ω-aminocarboxylic acid, a derivative thereof of formula (III) or a further derivative of one of the above (for example, an oligomerisation and or cyclisation compound starting from a derivative of formula (III)), in a composition comprising at least one lubricating base (base oil).

The disclosure is now further shown in the following examples, which are given purely by way of example and are not intended in any way as limiting the disclosure as described and claimed herein.

EXAMPLES

In the examples below, unless otherwise specified, reference is made to the following abbreviations and the following materials:

- Syngas (gaseous mixture of hydrogen and carbon monoxide in molar ratio 1:1 in pressurised cylinders): prod. SAPIO, IT;
- 9-methyl decenoate (9-DAME): purity >98%, prod. Elevance (Clean® 1000), (CAS 25601-41-6);
- (acetylacetonate)dicarbonylrhodium(I) ((acac)Rh(CO)$_2$): 98% purity, prod. Aldrich, cod. 288101 (CAS 14874-82-9, PM=258.03 Da);
- 6,6'-[(3,3'-Di-tert-butyl-5,5'-dimethoxy-1,1'-biphenyl-2,2'-diyl)bis(oxy)]-bis(dibenzo[d,f][1,3,2]dioxaphosphepin (BiPhePhos): purity: 97%, prod. Aldrich, cod. 699535 (CAS 121627-17-6, PM=786.78 Da);
- Methyl tert-butyl ether (solvent, MTBE): 99.8% purity, prod. Sigma-Aldrich;
- toluene: 99.8% purity, prod. Sigma-Aldrich;
- methanol: 99.8% purity, prod. Sigma-Aldrich;
- acetone: 99.8% purity.

Gas Chromatographic Analysis

The gas chromatographic analysis for the determination of reagents and products of the hydroformylation and reductive amination reactions is carried out with Agilent 7890B gas chromatograph, fitted with split/spliless injector and flame ionisation detector fitted with HP-1 column (100% polydimethylsiloxane, Agilent J&W), Fused Silica WCOT, 25m Length, 0.20 mm ID, 0.33 μm Film Thickness, Carrier Gas $H_2$, 0.8 ml/min, Constant Flow, 500:1 Split Ratio, Temperature injector 300° C., detector temperature 330° C., oven temperature program 40° C. to 8° C./min up to 320° C.

The quantification is performed with the internal standardisation method, by measuring the response factors of the available components with respect to n-dodecane (internal standard).

The sample is analysed by weighing accurately 0.5 g of sample and making up to volume, always weighing accurately, in a 2 mL vial with a solution of about 3000 ppm of n-dodecane in chloroform.

The examples specified refer to the batch mode (for laboratory simplicity), but are also representative of the corresponding continuous process.

Example 1: Hydroformylation of 9-DAME with Syngas in MTBE

Molar ester ratio/Rh=5065, L molar ratio (phosphinic)/Rh=16.

In a 500 ml autoclave fitted with mechanical stirrer, heating jacket and gas inlet, 102 g (0.542 mol) of 9-DAME, a 70 ml solution of MTBE, containing 28.3 mg (0.107 mmol) of (acac)Rh$(CO)_2$ and 1381 mg (1.703 mmol) of BiPhePhos, previously prepared in an inert atmosphere are introduced and stirred under a current of nitrogen for 1 h and an approximately additional 60 ml of MTBE are introduced.

The autoclave is flushed with syngas twice, then pressurised up to 3.0 MPa at room temperature and brought, under stirring, to the temperature of 100° C. (temperature at which the pressure inside the reactor is approximately 5.0 MPa).

The reaction continues for 2 hours, at the end of which the reactor is cooled and the liquid reaction mixture discharged and maintained as such in a nitrogen atmosphere.

From gas chromatographic analyses carried out in the presence of an internal standard, a conversion of 9-DAME of 99.9%, a selectivity towards hydroformylation products (oxoesters) of 76% and a l/b ratio between methyl 11-oxoundecanoate (ω-oxoester) and the sum of its branched isomers, equal to 53, is observed.

Example 2: Reductive Amination of Methyl 11-Oxoundecanoate

In a 250 ml autoclave fitted with mechanical stirrer, heating mantle, basket for the catalyst and inlet for the gases, 30 g of cobalt-based hydrogenation catalyst supported on alumina (HTC Co 2000 RP 1.2 mm, 15% of Co supported on alumina, commercial product Johnson Matthey Chemicals GmbH, D—data from U.S. Pat. No. 8,293,676 B2 Table 3 columns 21-22 Example J), is placed inside the dedicated catalyst holder and activated in a hydrogen atmosphere.

Activation of the catalyst is carried out by first subjecting it to flushing with nitrogen at atmospheric pressure, after which the reactor is heated to up to 150° C. with a temperature ramp of 25-50° C./h and, once this temperature has been reached, the hydrogen is fed at a flow rate of 30 ml/min, thus raising the temperature to up to 180° C.

At this point, the hydrogen flow rate is increased by progressively reducing the nitrogen flow rate until the gas flushing is completely hydrogen based (flow rate 200 ml/min). Under these temperature and flow conditions, activation continues for 18 hours, then proceeds by restoring the nitrogen current (and, at the same time, reducing that of hydrogen) in order to keep the catalyst in an inert atmosphere, progressively cooling the system down to room temperature.

The hydrogen is then discharged and 58 g (3.41 mol) of gaseous ammonia are introduced. The reactor is pressurised again with gaseous hydrogen to up to 3.8 MPa, then 57.8 g of the liquid reaction mixture obtained in example 1 above are loaded into it, containing 42% (24.3 g, 113.3 mmol) of methyl 11-oxoundecanoate, to which 58 g of MTBE and 4.7 g of water are added (8% by weight with respect to ammonia). The autoclave is then heated to up to 100° C. under stirring, reaching a pressure of 8.9 MPa. Once the desired temperature is reached, the reaction continues for 1 h before cooling and unloading the autoclave.

From the gas chromatographic analysis carried out on the reaction crude in the presence of an internal standard, a conversion of methyl 11-oxoundecanoate and other oxoesters to the corresponding 99% reductive amination products is observed: of these, 98% are aminoesters, whilst the products of reductive amination and contextual amidation (aminoamides) amount to 2%.

The saturated esters from the first hydroformylation stage remain as by-products, partially converted into the corresponding saturated amides.

Example 3: Hydrolysis of the Mixture of Aminoesters and Aminoamides of Example 2 and Purification of the 11-Amino-Undecanoic Acid Obtained In a 500 ml flask fitted with a stirrer, heating mantle and reflux condenser, g of a mixture of aminoesters and aminoamides in MTBE, obtained starting from the reaction crude of Example 2 by removal of part of the solvent (MTBE), are loaded by vacuum evaporation, containing 50.8% by mass of methyl 11-aminoundecanoate, to which approximately 300 ml of water and 45% NaOH are added until a pH of 12 is reached.

The mixture is heated up to boiling temperature under stirring and left under these conditions for 6 hours, under reflux. At the end of the hydrolysis, the mixture is cooled, then the pH is brought back to a value of 6 by adding hydrochloric acid.

The formation of a white precipitate is observed which is left to cold settle overnight. The solid is separated by vacuum filtration on a buchner funnel and washed repeatedly with water and with portions of cold acetone. 11-aminoundechaonic acid (12.7 g) is obtained as a very fine white solid and is characterised by nuclear magnetic resonance analysis at proton and carbon 13. The melting point is 181-183° C. The molar yield, calculated with respect to the linear aminoester (methyl 11-aminoundecanoate), is 76%.

Example 4: Hydroformylation of 9-DAME in Methanol with Syngas

In a 500 ml autoclave like that used in example 1 above, 25.4 g (0.135 moles) of 9-DAME are introduced in 210 ml of methanol and a solution containing 4.9 mg (0.0186 mmoles) of (acac)Rh$(CO)_2$ and 118 mg (0.145 mmoles) of BiPhePhos in 10 ml of methanol, previously prepared in an inert atmosphere and maintained under stirring under a current of nitrogen for 1 h. The autoclave is flushed with Syngas twice, then pressurised to up to 4.5 MPa whilst, under stirring, it is brought to a temperature of 100° C. The reaction continues for 2 hours, at the end of which the reactor is cooled and the reaction mixture discharged.

From gas chromatographic analyses carried out in the presence of an internal standard, a 9-DAME conversion of 99.9%, a selectivity towards hydroformylation products (oxoesters both in the form of free aldehydes and dimethylacetals) of 80% and a l/b ratio between linear compounds (methyl 11-oxoundecanoate+methyl 11,11-dimethoxy-undecanoate) and the sum of the corresponding branched isomers equal to 44, is observed. By acid hydrolysis of the reaction crude, carried out at pH 1 under reflux for 3 hours, the dimethylacetals can be converted into the corresponding oxoesters.

Example 5: Hydroformylation of 9-DAME with Syngas in MTBE

Molar ester ratio/Rh=4970, molar ratio L/Rh=16.

In a 500 ml autoclave like that used in example 1 above, 25.5 g (0.1356 mol) of 9-DAME, a solution of 35 ml of MTBE, containing 7.2 mg (0.0273 mmol) of $(acac)Rh(CO)_2$ and 349 mg (0.430 mmol) of BiPhePhos, previously prepared in an inert atmosphere and maintained under stirring under a current of nitrogen for 1 hour and approximately 185 ml of MTBE, are introduced. The autoclave is flushed with syngas twice, then pressurised up to 3.0 MPa (30 bar) at room temperature and brought, under stirring, to the temperature of 100° C. (temperature at which the pressure inside the reactor is approximately 5.0 Mpa (approximately 50 bar). The reaction continues for 2 hours, at the end of which the reactor is cooled and the liquid reaction mixture discharged and maintained as such in a nitrogen atmosphere.

From gas chromatographic analyses carried out in the presence of an internal standard, a conversion of 9-DAME of 99.9%, a selectivity towards hydroformylation products (oxoesters) of 71% and a l/b ratio between methyl 11-oxoundecanoate (ω-oxoester) and the sum of its branched isomers, equal to 55, is observed.

Example 6: Reductive Amination of Methyl 11-Oxoundecanoate

In a 250 ml autoclave like that used in example 2 above, 56 g (3.29 moles) of gaseous ammonia are charged at room temperature, in the presence of 30 g of hydrogenation catalyst based on Nickel supported on silica-alumina (Ni-3288 E 1/16" 3F, approximately 60% of Ni, commercial product of Engelhard De Meern B.V., NL) placed inside the dedicated catalyst holder and previously activated in a hydrogen atmosphere as already described in example 2 above for the cobalt hydrogenation catalyst. The reactor is pressurised with gaseous hydrogen to up to 3.8 MPa (38 bar), then 67.6 g of the mixture of oxoesters obtained as described in Example 5 above are introduced, after removing part of the reaction solvent (MTBE) by vacuum evaporation, containing 26.2% by mass (17.7 g, 82.9 mmol) of methyl 11-oxoundecanoate. 45 g of MTBE and 4 g of water are also supplied (7% by weight with respect to ammonia).

At the end of the loading of the oxoester solution in MTBE, the autoclave is heated to up to 108° C. under stirring, reaching a pressure of 8.4 MPa (84 bar). Once the desired temperature is reached, the reaction continues for 60 minutes (1 h) before cooling and unloading the autoclave.

From the gas chromatographic analysis carried out on the reaction crude in the presence of an internal standard, a full conversion of methyl 11-oxoundecanoate and other oxoesters to the corresponding reductive amination products is observed: of these, 98% are aminoesters, whilst the products of reductive amination and contextual amidation (aminoamides) amount to 2%. The saturated esters from the first hydroformylation stage remain as by-products, partially converted into the corresponding saturated amides.

Example 7: Hydroformylation of Methyl 9-Decenoate with Syngas in Toluene

T=100° C., syngas pressure=4.5 MPa, ester/Rh molar ratio=5000, L/Rh molar ratio=16.

In a 500 ml autoclave like that used in example 1 above, 25 g (0.133 mol) of methyl 9-decenoate are placed in 220 ml of dry toluene and a solution containing 7 mg (0.0266 mmol) of $(acac)Rh(CO)_2$ and 345 mg (0.425 mmol) of BiPhePhos in toluene, previously prepared in a dry box and stirred under nitrogen for 1 hour. The autoclave is flushed with syngas twice, then pressurised to up to 4.5 MPa and brought, under stirring, to a temperature of 100° C. The reaction continues for two hours, at the end of which the reactor is cooled and the reaction mixture discharged.

From gas chromatographic analyses carried out in the presence of an internal standard, a conversion of methyl 9-decenoate of 99.9%, a selectivity towards hydroformylation products (oxoesters) of 71% and al/b ratio between 11-oxoundecanoate of methyl (ω-oxoester) and the sum of its branched isomers equal to 66, is observed.

Example 8: Reductive Amination of Methyl 11-Oxoundecanoate in the Presence of Water, Feeding of Oxoester into the Reactor Already Pressurised with Hydrogen In a 250 ml autoclave like that used in example 2 above, 88 g (5.17 moles) of gaseous ammonia are charged at room temperature, in the presence of 30 g of hydrogenation catalyst based on Nickel supported on silica-alumina (Ni-3288 E 1/16" 3F, approximately 60% of Ni, commercial product of Engelhard De Meern B.V., NL) placed inside the dedicated catalyst holder and previously activated in a hydrogen atmosphere. The reactor is pressurised with gaseous hydrogen to up to 3.4 MPa (34 bar), then 32 g of the reaction mixture obtained in Example 7 are fed into it, after removing most of the reaction solvent (toluene) by evaporation under vacuum, containing 57% by mass (18.2 g, 85.1 mmoles; ammonia/oxoester ratio=60) of methyl 11-oxoundecanoate, with the addition of 93 g of methanol and 4.7 g of water (5.3% by weight with respect to ammonia).

At the end of the loading of the oxoester methanolic solution, the autoclave is heated to up to 108° C. under stirring, reaching a pressure of 8.2 MPa (82 bar). Once the desired temperature is reached, the reaction continues for 60 minutes before cooling and unloading the autoclave.

From the gas chromatographic analysis carried out on the reaction crude in the presence of an internal standard, a full conversion of methyl 11-oxoundecanoate and other oxoesters to the corresponding reductive amination products is observed: of these, 88% are aminoesters, whilst the products of reductive amination and contextual amidation (aminoamides) amount to 12%. The saturated esters from the first hydroformylation stage remain as by-products, partially converted into the corresponding saturated amides.

Example 9: Hydrolysis of Methyl 11-Amino-Undecanoate from Example 8 and Purification of the 11-Amino-Undecanoic Acid Obtained In a 500 ml flask such as that used in example 3 above, 26.2 g of a mixture of aminoesters and aminoamides in methanol, obtained starting from the reaction raw product from example 8 by removal of part of the solvent (methanol), are loaded by vacuum evaporation, containing 50% by mass of methyl 11-aminoundecanoate, to which approximately 300 ml of water and 40% NaOH are added until a pH of 12 is reached. The mixture is heated up to boiling temperature under stirring and left under these conditions for 6 hours, under reflux. At the end of the hydrolysis, the mixture is cooled, then the pH is brought back to a value of 6 by adding hydrochloric acid.

The formation of a white precipitate is observed which is left to cold settle overnight. The solid is separated by vacuum filtration on a buchner funnel and washed repeatedly with portions of cold acetone.

11-aminoundechaonic acid (10.4 g) is obtained as a very fine white solid and is characterised by nuclear magnetic resonance analysis at proton and carbon 13. The melting point is 180-184° C. The molar yield, calculated with respect to the linear aminoester (methyl 11-aminoundecanoate), is 85%.

Tables 1 and 2 show the summary data of the above examples.

Lastly, it is understood that further modifications and variants not specifically mentioned in the text may be made to the process, as described and illustrated herein, which, however, are to be considered as obvious variants of the present disclosure within the scope of the appended claims.

TABLE 1

| hydroformylation tests | | | | | | | | |
|---|---|---|---|---|---|---|---|---|
| Example | 9-DAME (g) | 9-DAME/Rh (mol/mol) | BiPhePhos/Rh (mol/mol) | solvent | temperature (° C.) | pressure (MPa) | yield to ω-oxo-ester (%) | Selectivity towards linear product (l/b) |
| 1 | 102 | 5065 | 16 | MTBE | 100 | 5.0 | 75 | 53:1 |
| 4 | 25.4 | 7260 | 8 | methanol | 100 | 4.5 | 78 | 44:1 |
| 5 | 25.5 | 4970 | 16 | MTBE | 100 | 5.0 | 71 | 55:1 |
| 7 | 25 | 5000 | 16 | toluene | 100 | 4.5 | 70 | 66:1 |

TABLE 2

| reductive amination tests | | | | | | | | | |
|---|---|---|---|---|---|---|---|---|---|
| Example | substrate (ref.) | mol $NH_3$/ mol ω-oxo-ester (—) | water (% w/w with respect to $NH_3$) | solvent | Cat. (metal supported on Si/Al) | temperature (° C.) | pressure (MPa) | yield (1) (%) | Aminoesters/ aminoamides ratio |
| 2 | From example 1 (42% of ω-oxoester in MTBE) | 30 | 8 | MTBE | Co | 100 | 8.9 | 99 | 98:2 |
| 6 | From example 5 (26.2% of ω-oxoester in MTBE) | 40 | 7 | MTBE | Ni | 108 | 8.4 | 100 | 98:2 |
| 8 | From example 7 (57% of ω-oxoester in toluene) | 60 | 5.3 | methanol | Ni | 108 | 8.2 | 100 | 88:12 |

(1) Yield to all products of reductive amination

The invention claimed is:

1. A process for the preparation of an ω-aminocarboxylic acid or a derivative thereof of formula (III), starting from an ω-unsaturated carboxylic compound with the following formula (I):

$$H_2C{=}CR'\text{-}(Q)\text{-}COR'' \qquad (I)$$

wherein R' is H or an aliphatic hydrocarbon group, possibly substituted, with 1 to 10 carbon atoms;

R" is an OR or $NR^1R^2$ group, wherein R is selected from between H, ammonium, a monovalent M metal, a C1-C15 alkyl group and a C6-C15 aryl group;

$R^1$ and $R^2$ are independently selected from between H, a C1-C15 alkyl group and a C6-C15 aryl group;

Q is a divalent, aliphatic, optionally substituted hydrocarbon group with 1 to 12 carbon atoms, and, furthermore, said R' and Q groups can be linked together to form an aliphatic carbocyclic structure with 5 to 7 carbon atoms;

said process comprising the following stages in sequence:

(A) making said compound of formula (I) react under the hydroformylation conditions with a mixture of hydrogen and carbon monoxide in the presence of a hydroformylation catalyst, based on rhodium (I) and phosphine binders and, optionally, a solvent, to obtain the corresponding ω-oxocarboxylic derivative with the following formula (II):

$$HOC{-}CH_2{-}CHR'\text{-}(Q)\text{-}COR'' \qquad (II)$$

with R', R" and Q correspondingly having the meaning specified above, (B) subjecting said compound of formula (II) as obtained in step (A), in the absence of intermediate purification steps of the compound of formula (II) from the other reaction products, to reductive amination by reaction with hydrogen and ammonia in the presence of a catalyst to obtain the ω-aminocarboxylic derivative of formula (III):

$$H_2N{-}CH_2{-}CH_2{-}CHR'\text{-}(Q)\text{-}COR'' \qquad (III)$$

and separating it from any reaction solvent;

(C) optionally subjecting said compound of formula (III) to hydrolysis to obtain the corresponding ω-aminocarboxylic acid wherein R" in formula (III) is OH.

2. The process according to claim 1, wherein the hydroformylation reaction in said step (A) is carried out at a temperature of between 6° and 140° C. and at a pressure of between 1.5 and 6 MPa, in a solvent selected from between an ether, an alcohol or an aromatic solvent.

3. The process according to claim 1, wherein the hydroformylation reaction in said step (A) is carried out in the presence of a catalyst comprising a ligand comprising at least one phosphine and a soluble salt or complex of a metal selected from the group consisting of Rhodium, Cobalt, Iridium, and Ruthenium.

4. The process according to claim 3, wherein said catalyst comprises a rhodium complex selected from between $HRh(CO)(PPh_3)_3$, $(acac)Rh(CO)_2$, $[Rh(COD)Cl]_2$ and a bidentate or polidentate phosphine.

5. The process according to claim 1, wherein the reaction mixture obtained in step (A) is transferred to step (B) without carrying out any separation step except for the evaporation of at least a part of the possible solvent and recovery of the catalyst with one of the methods known in literature.

6. The process according to claim 1, wherein said reductive amination stage (B) is carried out with ammonia in the presence of hydrogen at a temperature of between 30 and 200° C., and at a pressure between 3 and 15 MPa.

7. The process according to claim 1, wherein said reductive amination step (B) is carried out in the presence of a catalyst comprising cobalt or nickel.

8. The process according to claim 1, wherein, in said stage (B), ammonia and hydrogen are in an $NH_3/H_2$ molar ratio of between 5 and 25.

9. The process according to claim 1, wherein, in the compound of formula (III) obtained in step (B), R" is an —OR group with R═C1-C5 alkyl and said hydrolysis step (C) is carried out in an aqueous environment, in the presence of an acidic or basic catalyst.

10. The process according to claim 1, wherein said ω-unsaturated carboxylic compound of formula (I) is an ester of 9-decenoic acid.

11. The process according to claim 1, for the preparation of 11-aminoundecanoic acid.

12. A lubricating composition comprising a base oil and at least one additive wherein said additive and/or said base oil is a ω-aminocarboxylic acid of formula (III) or a derivative thereof of formula (III), said ω-aminocarboxylic acid of formula (III) and/or said derivative thereof of formula (III) being obtained according to the process recited in claim 1.

13. The lubricating composition according to claim 12, wherein said ω-aminocarboxylic acid or a derivative thereof of formula (III) derives from an ω-unsaturated carboxylic compound of formula (I) of renewable origin, starting from methyl 9-decenoate (9-DAME) obtained from the reaction of metathesis of vegetable oils and fats from renewable sources.

14. A bio-lubricant according to claim 13, where a percentage content of carbon from renewable raw materials on the entire formulation is at least one percent (1%) by weight and derives from ω-aminocarboxylic acid of formula (III) or a derivative thereof of formula (III).

15. A bio-lubricant according to claim 13, where a percentage content of carbon from renewable raw materials is at least 25% by weight on a single component from ω-aminocarboxylic acid and derives from the ω-aminocarboxylic acid of formula (III) or a derivative thereof of formula (III).

16. The bio-lubricant according to claim 15, wherein said percentage content of carbon from renewable raw materials is at least 50%.

17. A method for the preparation of a lubricating or biolubricating composition comprising the preparation of an ω-aminocarboxylic acid of formula (III) or a derivative thereof of formula (III) according to the process according to claim 1 and, in addition, the additional step and subsequent to introduce said ω-aminocarboxylic acid, a derivative thereof of formula (III) or a further derivative of one of the above, in a composition comprising at least one lubricating base (base oil).

18. The process according to claim 1, wherein the hydroformylation catalyst is based on rhodium (I) and phosphine binders.

19. The process according to claim 1, wherein step (B) is in the absence of intermediate purification steps of the compound of formula (II) from the other reaction products.

20. The process according to claim 2, wherein the hydroformylation reaction is carried out in a solvent selected from between an ether, an alcohol or an aromatic solvent.

21. The lubricating composition according to claim 13, wherein said ω-aminocarboxylic acid or a derivative thereof of formula (III) derives from methyl 9-decenoate (9-DAME) obtained from the reaction of metathesis of vegetable oils and fats from renewable sources.

* * * * *